US006248391B1

(12) United States Patent
Grillo et al.

(10) Patent No.: US 6,248,391 B1
(45) Date of Patent: *Jun. 19, 2001

(54) BRIGHT WHITE FILM COATINGS AND FILM COATING COMPOSITIONS THEREFOR

(75) Inventors: Susan M. Grillo; Brian Korchok, both of Lansdale; Bruce Kinsey, Harleysville; Melanie Hartman, Souderton; Stuart C. Porter, Hatfield; Rita Steffenino, Green Lane; George Reyes, North Wales; Thomas J. Burke, Plymouth Meeting, all of PA (US)

(73) Assignee: BPSI Holdings, Inc., Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/895,484

(22) Filed: Jul. 16, 1997

(51) Int. Cl.$^7$ .............................. B05D 5/06; A61K 9/28
(52) U.S. Cl. ................ 427/2.23; 427/2.14; 426/572; 424/441; 424/462; 424/481; 424/458
(58) Field of Search .................. 427/2.14, 2.23; 424/479, 474, 439, 440, 441, 442, 463, 480, 481, 482, 458; 426/572

(56) References Cited

U.S. PATENT DOCUMENTS

| | | | |
|---|---|---|---|
| 3,420,931 | * 1/1969 | Daum et al. ..................... 427/2.18 |
| 3,882,228 | * 5/1975 | Boncy et al. ..................... 427/2.14 |
| 4,059,460 | * 11/1977 | Schollmeier et al. ................. 127/29 |
| 4,238,510 | * 12/1980 | Cherukuri et al. ..................... 426/5 |
| 4,543,370 | * 9/1985 | Porter et al. .......................... 523/100 |
| 4,610,891 | * 9/1986 | Miyamoto et al. ..................... 424/35 |
| 4,652,313 | 3/1987 | Den Boer et al. . |
| 4,802,924 | * 2/1989 | Woznicki et al. ................... 427/2.15 |
| 4,816,298 | * 3/1989 | Alderman et al. ................... 427/2.14 |
| 4,837,031 | * 6/1989 | Denton ................................. 424/464 |
| 4,882,160 | * 11/1989 | Yang et al. ............................ 424/440 |
| 5,037,410 | * 8/1991 | Zimmerman et al. ................ 604/358 |
| 5,039,540 | * 8/1991 | Ecanow ................................. 426/385 |
| 5,171,589 | * 12/1992 | Richey et al. ............................ 426/5 |
| 5,370,881 | * 12/1994 | Fuisz ........................................ 426/5 |
| 5,603,953 | * 2/1997 | Herbig et al. ......................... 424/473 |
| 5,641,536 | * 6/1997 | Lech et al. ........................... 427/2.14 |
| 5,882,707 | * 3/1999 | Grillo et al. .......................... 426/305 |

\* cited by examiner

*Primary Examiner*—Shrive Beck
*Assistant Examiner*—Jennifer Kolb
(74) *Attorney, Agent, or Firm*—Roberts & Mercanti, LL

(57) ABSTRACT

A dry film coating composition used to make a bright white film coating for nutritional supplements, pharmaceutical tablets, and the like, comprises dextrose, an auxiliary film-former, and titanium dioxide. Optionally, but advantageously, the coating composition also may include one or more of the following components: a plasticizer, a surfactant, a flow aid, and a preservative.

14 Claims, No Drawings

BRIGHT WHITE FILM COATINGS AND FILM COATING COMPOSITIONS THEREFOR

BACKGROUND OF THE INVENTION

1. Field of the Invention

This invention relates to the field of aqueous film coating of nutritional supplements and pharmaceutical tablets, and is specifically concerned with providing bright white film coatings based on dextrose for coating nutritional supplements, such as vitamin tablets and calcium/oyster shell tablets, and pharmaceutical tablets, such as acetaminophen (APAP), aspirin (ASA), and Ibuprofen.

2. Description of the Prior Art

Hydroxypropyl methylcellulose (HPMC) has been used in coatings for substrates such as pharmaceutical tablets. For example, such coatings, including white coatings (coatings containing titanium dioxide as the colorant), made from coating compositions manufactured by Colorcon and disclosed in U.S. Pat. Nos. 4,543,370 and 4,683,256, said patents being incorporated herein by reference, have proven especially effective when used on pharmaceutical tablets.

However, in the pharmaceutical and nutritional supplement industries, it is desired to provide some pharmaceuticals, such as APAP and Ibuprofen, and some nutritional supplements with a white coating that is brighter than the white coatings obtained using HPMC-based coating compositions.

SUMMARY OF THE INVENTION

It is an object of the invention to provide a white film coating for vitamin tablets, calcium/oyster shell tablets, and pharmaceutical tablets that is brighter than the white film coatings obtained using HPMC-based coating compositions.

These and other objects are accomplished by our invention, which is described below.

DETAILED DESCRIPTION OF THE INVENTION

In accordance with the invention, our dry film coating compositions for use in forming coating dispersions for film coating nutritional supplements, pharmaceutical tablets, and the like, comprise dextrose, an auxiliary film former, and titanium dioxide.

Advantageously, the inventive dry film coating compositions may include one or more of the following components: a plasticizer, a surfactant, a flow aid, and a preservative.

In accordance with the invention, a method of coating substrates such as nutritional supplements, pharmaceutical tablets, and the like, comprises mixing dextrose, an auxiliary film-former, and titanium dioxide into water to form an inventive aqueous coating dispersion, applying the inventive coating dispersion onto said substrates to form a white film coating on said substrates, and drying the white film coating on said substrates. Optionally, but advantageously, the following components may be mixed into water with the dextrose, the auxiliary film-former, and the titanium dioxide to form the inventive coating dispersion: a plasticizer, a surfactant, a flow aid, and a preservative.

The invention also includes the coated substrates, such as coated vitamins, coated calcium/oyster shell tablets, and coated pharmaceutical tablets, the aqueous coating dispersion formed from the inventive dry film coating composition or from the components of said composition, the method of making the dry film coating compositions and the method of making the coating dispersions of the invention.

The primary film-former of the inventive dry film coating composition and of the inventive aqueous coating dispersion is dextrose.

The preferred range for dextrose is about 20% to about 50% by weight of the inventive dry film coating composition and of the non-water ingredients of the inventive aqueous coating dispersion. More preferably, the range for dextrose is about 25% to about 35% by weight of the inventive dry film coating composition and of the non-water ingredients of the inventive aqueous coating dispersion.

The auxiliary film-former may be polyvinylpyrrolidone (PVP), hydroxypropyl methylcellulose, methylcellulose, hydroxypropyl cellulose (HPC), sodium carboxymethylcellulose (sodium CMC), maltodextrin, polydextrose, modified food starch, modified food starch with corn syrup solids, starch (e.g., STARCH 1500 starch), tapioca dextrin, lactose, sodium alginate, PG alginate, gum acacia, polyvinyl alcohol (PVA), any of the film coating polymers recited in Colorcon U.S. Pat. No. 4,543,370, which is incorporated herein by reference, and combinations thereof. The auxiliary film-former(s) act as strength enhancers for the film coating. Their presence in the coatings help prevent cracking of the film coating, as well as helping to prevent edge wear/chipping of the coated tablet. A preferred auxiliary film-former is sodium CMC. The preferred and the more preferred ranges for the auxiliary film-former(s) by weight of the inventive dry film forming composition and by weight of the non-water ingredients of the inventive aqueous coating dispersion are 1% to 50% (preferred) and 10% to 20% (more preferred). The preferred ranges and the more preferred ranges for various exemplary auxiliary film-former(s) are set out below.

The preferred range and the more preferred range for the titanium dioxide ($TiO_2$) are 25% to 50% (preferred) and 30% to 40% (more preferred) by weight of the inventive coating composition and by weight of the non-water ingredients of the inventive coating dispersion.

Exemplary of the plasticizer are mineral oil, polyethylene glycol having a molecular weight in the range of 200 to 8000, propylene glycol, glycerine, triacetin, acetyltriethyl citrate, triethyl citrate (Citroflex A2), tributylcitrate (Citroflex 4), and acetyltributylcitrate (Citroflex A4), and the preferred ranges for the plasticizer are set out below, together with preferred and more preferred ranges for various exemplary plasticizers.

Exemplary of the surfactant is Polysorbate 80, and the preferred ranges for the surfactant are set out below, together with preferred and more preferred ranges for an exemplary surfactant.

Exemplary of the flow aid is stearic acid, and the preferred ranges and the more preferred ranges for the flow aid are set out below, together with the preferred and the more preferred ranges for stearic acid.

Exemplary of the preservative is sodium citrate, and the preferred ranges for the preservative are set out below, together with the preferred and the more preferred ranges for sodium citrate.

| AUXILIARY FILM FORMERS | |
| --- | --- |
| Preferred | 1–50% |
| More Preferred | 10–20% |
| PVA | |
| Preferred | 0–10% |
| More Preferred | 3–6% |
| PVP | |
| Preferred | 0–10% |
| More Preferred | 3–6% |
| HPMC/Methylcellulose/HPC | |
| Preferred | 0–50% |
| More Preferred | 5–50% |
| Even More Preferred | 10–20% |
| Polydextrose | |
| Preferred | 0–50% |
| More Preferred | 5–50% |
| Even More Preferred | 10–20% |
| Lactose | |
| Preferred | 0–20% |
| More Preferred | 5–10% |
| Na CMC | |
| Preferred | 0–15% |
| More Preferred | 1–15% |
| Even More Preferred | 5–8% |
| Modified Food Starch/ | |
| Modified Food Starch with Corn Syrup Solids/Starch 1500 | |
| Preferred | 0–15% |
| More Preferred | 1–15% |
| Even More Preferred | 5–8% |
| Maltodextrin | |
| Preferred | 0–50% |
| More Preferred | 5–50% |
| Even More Preferred | 10–20% |
| Tapioca Dextrin | |
| Preferred | 0–5% |
| More Preferred | 1–5% |
| Even More Preferred | 3–5% |
| PG Alginate | |
| Preferred | 0–5% |
| More Preferred | 3–5% |
| Sodium Alginate | |
| Preferred | 0–5% |
| More Preferred | 3–5% |
| Gum Acacia | |
| Preferred | 0–5% |
| More Preferred | 3–5% |
| SURFACTANT | |
| Preferred | 0–5% |
| Polysorbate 80 | |
| Preferred | 0–5% |
| More Preferred | 0.5–1% |
| FLOW AID | |
| Preferred | 0–15% |
| More Preferred | 5–10% |
| Stearic Acid | |
| Preferred | 0–15% |
| More Preferred | 5–10% |
| PLASTICIZER | |
| Preferred | 0–20% |

-continued

| | |
| --- | --- |
| Mineral Oil | |
| Preferred | 0–15% |
| More Preferred | 3–5% |
| Polyethylene Glycol 8000 | |
| Preferred | 0–20% |
| More Preferred | 5–10% |
| Glycerine | |
| Preferred | 0–15% |
| More Preferred | 5–10% |
| PRESERVATIVE | |
| Preferred | 0–5% |
| More Preferred | 2–3% |
| Sodium Citrate | |
| Preferred | 0–5% |
| More Preferred | 2–3% |

The ranges set out above are all by weight of the dry film coating composition of the invention and of the non-water ingredients of the aqueous coating dispersion of the invention.

The following examples illustrate the invention, all ingredients being by weight.

EXAMPLE 1

The dry components of the following formulation were blended together for five minutes in a PK Blender (Paterson Kelly) to form a mixture. Then, the liquid components were added to the mixture of dry components via the I-bar of the blender and blended therein by mixing for an additional five minutes to form a dry film coating composition of the invention.

Optionally, the composition may be milled such as in a hammer mill (Apex Machinery, Dartford, England), for example.

Optionally, the dry film coating composition may be granulated using a planetary mixer, such as a Hobart planetary mixer. To accomplish this, the dry film coating composition is loaded into the mixer and the mixer is switched on, and sufficient water is slowly added until the composition forms slightly adherent granules. These granules are then passed through a 1–2 mm screen and then dried in a 30° C. oven until the moisture content is below 5%. The composition is then sieved again through a 1–2 mm screen and is then ready for use in a non-dusting, granular form. Other methods of granulation, such as spray granulation and roller compaction, also may be used.

450 grams of the resulting film coating composition was dispersed into 1800 grams of distilled water (about 30 minutes) to form an inventive coating dispersion (20% solids), and all of the dispersion was sprayed using a 24" Accela Cota coater (Thomas Engineering) onto 15000 grams of vitamin tablets (Pharmavite) to form an inventive coating thereon having a theoretical weight gain of 3.0%.

This produced a bright white film coating on the tablets.

| Component | Percentages | Grams |
| --- | --- | --- |
| Dextrose (Staley) | 32.0% | 1600.00 |
| HPMC/Pharmacoat E-50 (DOW/ShinEtsu) | 10% | 500.00 |
| Polyethylene Glycol 8000 | 8% | 400.00 |

-continued

| Component | Percentages | Grams |
|---|---|---|
| (Union Carbide) | | |
| HPMC/Pharmacoat E-15 (DOW/ShinEtsu) | 5% | 250.00 |
| Sodium CMC (Aqualon) | 6% | 300.00 |
| Sodium Citrate, Anhydrous (ADM Corn Processing) | 3% | 150.00 |
| Mineral Oil (Pennreco) | 3% | 150.00 |
| Titanium dioxide (water) (Kronos) | 32% | 1600.00 |
| Polysorbate 80 (ICI Surfactants) | 1% | 50.00 |
| | 100% | 5000.00 |

EXAMPLE 2

Example 1 was repeated, except that the dispersion was sprayed onto 15000 grams of APAP tablets. This produced a bright white film coating on the APAP tablets.

EXAMPLE 3

Example 1 was repeated, except that the film coating composition had the following formulation:

| Component | Percentages | Grams |
|---|---|---|
| Dextrose (Staley) | 26.0% | 1300.00 |
| HPMC/Pharmacoat E-50 (DOW/ShinEtsu) | 10% | 500.00 |
| Polyethylene Glycol 400 (Union Carbide) | 8% | 400.00 |
| HPMC/Pharmacoat E-15 (DOW/ShinEtsu) | 5% | 250.00 |
| Sodium CMC (Aqualon) | 6% | 300.00 |
| Stearic Acid (Humco) | 6% | 300.00 |
| Sodium Citrate, Anhydrous (ADM Corn Processing) | 3% | 150.00 |
| Mineral Oil (Pennreco) | 3% | 150.00 |
| Titanium dioxide (water) (Kronos) | 32% | 1600.00 |
| Polysorbate 80 (ICI Surfactants) | 1% | 50.00 |
| | 100% | 5000.00 |

This produced a bright white film coating on the tablets.

EXAMPLE 4

Example 2 was repeated, except that the film coating composition had the formulation of Example 3. This produced a bright white film coating on the APAP tablets.

EXAMPLE 5

The dry components of the following formulation were blended together for five minutes in a food processor to form a mixture. Then, the liquid components of the formulation were added to the mixture of the dry components and blended therein by mixing for an additional five minutes to form a film coating composition of the invention.

Optionally, the coating composition may be granulated or milled.

9.0 grams of the resulting film coating composition was dispersed into 36.0 grams of distilled water and stirred until dispersed to form an inventive coating dispersion (20% solids), and all of the dispersion was sprayed using an Aeromatic Strea 1 coater (Niro) onto 300 grams of ⅜" concave white placebos to form an inventive coating thereon having a theoretical weight gain of 3.0%.

This produced a bright white film coating on the tablets.

| Component | Percentages | Grams |
|---|---|---|
| Dextrose (Staley) | 26.0% | 1300.00 |
| HPMC/Pharmacoat E-50 (DOW/ShinEtsu) | 10% | 500.00 |
| Polyethylene Glycol 400 (Union Carbide) | 8% | 400.00 |
| HPMC/Pharmacoat E-15 (DOW/ShinEtsu) | 5% | 250.00 |
| Sodium CMC (Aqualon) | 6% | 300.00 |
| Stearic Acid (Humco) | 6% | 300.00 |
| Sodium Citrate, Anhydrous (ADM Corn Processing) | 3% | 150.00 |
| Mineral Oil (Pennreco) | 3% | 150.00 |
| Titanium dioxide (water) (Kronos) | 32% | 1600.00 |
| Polysorbate 80 (ICI Surfactants) | 1% | 50.00 |
| | 100% | 5000.00 |

Examples 6–19 further illustrate the invention, all percentages being by weight. In Examples 6–19, the components of each formulation are mixed together, formed into a coating dispersion, and applied to ⅜" concave white placebos, as in Example 5, to obtain bright white film coatings.

EXAMPLE 6

| Component | Percentages | Grams |
|---|---|---|
| Dextrose (Staley) | 35.0% | 1750.00 |
| HPMC/Pharmacoat E-50 (DOW/ShinEtsu) | 10% | 500.00 |
| Glycerin | 5% | 250.00 |
| HPMC/Pharmacoat E-15 (DOW/ShinEtsu) | 5% | 250.00 |
| Sodium CMC (Aqualon) | 6% | 300.00 |
| Sodium Citrate, Anhydrous (ADM Corn Processing) | 3% | 150.00 |
| Mineral Oil (Pennreco) | 3% | 150.00 |
| Titanium dioxide (water) (Kronos) | 32% | 1600.00 |
| Polysorbate 80 (ICI Surfactants) | 1% | 50.00 |
| | 100% | 5000.00 |

EXAMPLE 7

| Component | Percentages | Grams |
|---|---|---|
| Dextrose (Staley) | 35.0% | 1750.00 |
| Methylcellulose | 15% | 750.00 |
| Glycerin (DOW) | 5% | 250.00 |
| Sodium CMC (Aqualon) | 6% | 300.00 |
| Sodium Citrate, Anhydrous (ADM Corn Processing) | 3% | 150.00 |
| Mineral Oil (Pennreco) | 3% | 150.00 |
| Titanium dioxide (water) (Kronos) | 32% | 1600.00 |
| Polysorbate 80 (ICI Surfactants) | 1% | 50.00 |
| | 100% | 5000.00 |

EXAMPLE 8

| Component | Percentages | Grams |
|---|---|---|
| Dextrose (Staley) | 20.0% | 200.00 |
| Methylcellulose | 14% | 140.00 |
| Sodium CMC (Aqualon) | 8% | 80.00 |
| Stearic Acid (Humco) | 8% | 80.00 |
| Tapioca Dextrin (Staley) | 5% | 50.00 |
| Glycerin (DOW) | 2% | 20.00 |
| Sodium Citrate, Anhydrous (ADM Corn Processing) | 3% | 30.00 |
| Titanium dioxide (water) (Kronos) | 40% | 400.00 |
| | 100% | 1000.00 |

EXAMPLE 9

| Component | Percentages | Grams |
|---|---|---|
| Dextrose (Staley) | 20.0% | 200.00 |
| Methylcellulose (DOW) | 14% | 140.00 |
| Tapioca Dextrin (Staley) | 5% | 50.00 |
| Sodium CMC (Aqualon) | 8% | 80.00 |
| Polydextrose (Pfizer) | 8% | 80.00 |
| Glycerin (DOW) | 2% | 20.00 |
| Sodium Citrate, Anhydrous (ADM Corn Processing) | 3% | 30.00 |
| Titanium dioxide (water) (Kronos) | 40% | 400.00 |
| | 100% | 1000.00 |

EXAMPLE 10

| Component | Percentages | Grams |
|---|---|---|
| Dextrose (Staley) | 25.0% | 250.00 |
| Methylcellulose (DOW) | 14.0% | 140.00 |
| Sodium CMC (Aqualon) | 8% | 80.00 |
| PURITY 4* (National Starch and Chemical Company) | 8% | 80.00 |
| Glycerin (DOW) | 2% | 20.00 |
| Sodium Citrate, Anhydrous (ADM Corn Processing) | 3% | 30.00 |
| Titanium dioxide (water) (Kronos) | 40% | 400.00 |
| | 100% | 1000.00 |

*Purity 4 is a modified food starch with Tapioca as its source.

EXAMPLE 11

| Component | Percentages | Grams |
|---|---|---|
| Dextrose (Staley) | 25.0% | 250.00 |
| Methylcellulose (DOW) | 14.0% | 140.00 |
| Sodium CMC (Aqualon) | 8% | 80.00 |
| PURITY HO** (National Starch and Chemical Company) | 8% | 80.00 |
| Glycerin (DOW) | 2% | 20.00 |
| Sodium Citrate, Anhydrous (ADM Corn Processing) | 3% | 30.00 |
| Titanium dioxide (water) (Kronos) | 40% | 400.00 |
| | 100% | 1000.00 |

**Purity HO is modified Food Starch and dried Glucose Syrup with waxy maize as its source.

EXAMPLE 12

| Component | Percentages | Grams |
|---|---|---|
| Dextrose (Staley) | 25.0% | 250.00 |
| Methycellulose (DOW) | 14.0% | 140.00 |
| Sodium CMC (Aqualon) | 8% | 80.00 |
| PURITY GUM 59*** (National Starch and Chemical Company) | 8% | 80.00 |
| Glycerin (DOW) | 2% | 20.00 |
| Sodium Citrate, Anhydrous (ADM Corn Processing) | 3% | 30.00 |
| Titanium dioxide (water) (Kronos) | 40% | 400.00 |
| | 100% | 1000.00 |

***Purity GUM 59 is a modified food starch with waxy maize as its source

EXAMPLE 13

| Component | Percentages | Grams |
|---|---|---|
| Dextrose (Staley) | 29.0% | 1450.00 |
| HPMC/Pharmacoat E-50 (DOW/ShinEtsu) | 10% | 500.00 |
| Polyethylene Glycol 8000 (Union Carbide) | 8% | 400.00 |
| HPMC/Pharmacoat E-15 (DOW/ShinEtsu) | 5% | 250.00 |
| Sodium CMC (Aqualon) | 6% | 300.00 |
| Sodium Citrate, Anhydrous (ADM Corn Processing) | 3% | 150.00 |
| Mineral Oil (Pennreco) | 3% | 150.00 |
| Gum Acacia (Colloides Naturels, Inc.) | 3% | 150.00 |
| Titanium dioxide (water)(Kronos) | 32% | 1600.00 |
| Polysorbate 80 (ICI Surfactants) | 1% | 50.00 |
| | 100.0% | 5000.00 |

EXAMPLE 14

| Component | Percentages | Grams |
|---|---|---|
| Dextrose (Staley) | 25.0% | 250.00 |
| Methylcellulose (Dow) | 14.0% | 140.00 |
| Sodium CMC (Aqualon) | 8.0% | 80.00 |
| Starch 1500 (Colorcon) | 8.0% | 80.00 |
| Glycerin (Dow) | 2.0% | 20.00 |
| Sodium Citrate, Anhydrous (ADM Corn Processing) | 3.0% | 30.00 |
| Titanium dioxide (water) (Kronos) | 40.0% | 400.00 |
| | 100.0% | 1000.00 |

EXAMPLE 15

| Component | Percentages | Grams |
| --- | --- | --- |
| Dextrose (Staley) | 29.0% | 1450.00 |
| HPMC/Pharmacoat E-50 (DOW/ShinEtsu) | 10% | 500.00 |
| Polyethylene Glycol 8000 (Union Carbide) | 8% | 400.00 |
| HPMC/Pharmacoat E-15 (DOW/ShinEtsu) | 5% | 250.00 |
| Sodium CMC (Aqualon) | 6% | 300.00 |
| Sodium Citrate, Anhydrous (ADM Corn Processing) | 3% | 150.00 |
| Mineral Oil (Pennreco) | 3% | 150.00 |
| PG Alginate (Kelco) | 3% | 150.00 |
| Titanium dioxide (water)(Kronos) | 32% | 1600.00 |
| Polysorbate 80 (ICI Surfactants) | 1% | 50.00 |
| | 100.0% | 5000.00 |

EXAMPLE 16

| Component | Percentages | Grams |
| --- | --- | --- |
| Dextrose (Staley) | 29.0% | 1450.00 |
| HPMC/Pharmacoat E-50 (DOW/ShinEtsu) | 10% | 500.00 |
| Polyethylene Glycol 8000 (Union Carbide) | 8% | 400.00 |
| HPMC/Pharmacoat E-15 (DOW/ShinEtsu) | 5% | 250.00 |
| Sodium CMC (Aqualon) | 6% | 300.00 |
| Sodium Citrate, Anhydrous (ADM Corn Processing) | 3% | 150.00 |
| Mineral Oil (Pennreco) | 3% | 150.00 |
| Sodium Alginate (Kelco) | 3% | 150.00 |
| Titanium dioxide (water)(Kronos) | 32% | 1600.00 |
| Polysorbate 80 (ICI Surfactants) | 1% | 50.00 |
| | 100.00 | 5000.00 |

EXAMPLE 17

| Component | Percentages | Grams |
| --- | --- | --- |
| Dextrose (Staley) | 40% | 480.00 |
| HPMC/Pharmacoat E-15 (DOW/ShinEtsu) | 28% | 280.00 |
| Titanium Dioxide (water) (Kronos) | 32% | 320.00 |
| | 100% | 1000.00 |

EXAMPLE 18

| Component | Percentages | Grams |
| --- | --- | --- |
| Dextrose (Staley) | 40% | 400.00 |
| HPMC/Pharmacoat E-15 (DOW/ShinEtsu) | 18% | 180.00 |
| PEG 8000 | 10% | 100.00 |
| Titanium Dioxide (water) (Kronos) | 32% | 320.00 |
| | 100% | 1000.00 |

EXAMPLE 19

| Component | Percentages | Grams |
| --- | --- | --- |
| Dextrose (Staley) | 29.9% | 299.0 |
| HPMC/Pharmacoat E-15 (DOW/ShinEtsu) | 10.0% | 100.0 |
| Polyethylene Glycol 8000 (Union Carbide) | 8.0% | 80.0 |
| HPMC/Pharmacoat E-50 (DOW/ShinEtsu) | 5.0% | 50.0 |
| Sodium CMC (Aqualon) | 8.0% | 80.0 |
| Mineral Oil (Pennreco) | 3.0% | 30.0 |
| Sodium Citrate, Anhydrous (ADM Corn Processing) | 3.0% | 30.0 |
| Tapioca dextrin (Staley) | 0.1% | 1.0 |
| Titanium dioxide (water)(Kronos) | 32.0% | 320.0 |
| Polysorbate 80 (ICI Surfactants) | 1.0% | 10.0 |
| | 100.0% | 1000.0 |

EXAMPLE 20

Example 1 was repeated, except that the dispersion was sprayed onto 15000 grams of oyster shell substrates. This produced a bright white film coating on the oyster shell substrates.

Although it is preferred to make the coating dispersions of the invention from the inventive dry film coating compositions, the inventive coating dispersions may be made by adding the individual components of the inventive dry film coating composition to water to form the inventive coating dispersions.

Advantages

The invention provides a film coating that possesses good film adhesion and a smooth surface.

Moreover, the invention produces a bright white film coating that is noticeably brighter than white film coatings produced using HPMC-based coating compositions.

What is claimed is:

1. A method of coating substrates with a white film coating comprising the steps of
   mixing a primary film-former comprising dextrose, an auxiliary film-former, sodium citrate and titanium dioxide into water to form an aqueous coating dispersion,
   applying an effective amount of said aqueous coating dispersion onto said substrates to form a white film coating on said substrates, and
   drying the white film coating on said substrates.

2. The method of claim 1, including dispersing a plasticizer into the aqueous coating dispersion.

3. The method of claim 1, including dispersing a surfactant into the aqueous coating dispersion.

4. The method of claim 1, including dispersing a flow aid into the aqueous coating dispersion.

5. The method of claim 1, including dispersing a preservative into the aqueous coating dispersion.

6. The method of claim 1,
   the dextrose being in a range of about 20% to about 50% by weight of the non-water ingredients of the dispersion,
   the auxiliary film-former being in a range of about 1% to about 50% by weight of the non-water ingredients of the dispersion, and
   the titanium dioxide being in a range of about 25% to about 50% by weight of the non-water ingredients of the dispersion.

7. The method of claim 1, the dextrose being in a range of about 25% to about 35% by weight of the non-water ingredients of the dispersion, the auxiliary film-former being in a range of about 10% to about 20% by weight of the non-water ingredients of the dispersion, and the titanium dioxide being in a range of about 30% to about 40% by weight of the non-water ingredients of the dispersion.

8. The method of claim 6, further including a plasticizer, the plasticizer being mineral oil, polyethylene glycol, propylene glycol, glycerine, triacetin, acetyltriethyl citrate, triethyl citrate, tributylcitrate, or acetyltributylcitrate, and the plasticizer being in a range of greater than 0% to about 20% by weight of the non-water ingredients of the dispersion.

9. The method of claim 8, further including a surfactant, the surfactant being polysorbate 80, and the surfactant being in a range of greater than 0% to about 5% by weight of the non-water ingredients of the dispersion, a flow aid, the flow aid being stearic acid, and the flow aid being in a range of greater than 0% to about 15% by weight of the non-water ingredients of the dispersion, and a preservative, the preservative being sodium citrate, and the preservative being in a range of greater than 0% to about 5% by weight of the non-water ingredients of the dispersion.

10. The method of claim 1, wherein the sodium citrate is present in a range of from greater than 0% to about 5% by weight of the composition.

11. The method of claim 10, wherein the sodium citrate is present in a range of from about 2% to about 3% by weight of the composition.

12. A substrate coated by the process of claim 1.

13. The method of claim 1, wherein said substrate is a nutritional supplement.

14. The method of claim 1, wherein said substrate is a pharmaceutical tablet.

* * * * *